(12) United States Patent
Cauet et al.

(10) Patent No.: US 7,033,779 B1
(45) Date of Patent: Apr. 25, 2006

(54) METHOD FOR PREPARING STEROIDS MODIFIED BY YEAST FERMENTATION

(75) Inventors: Gilles Cauet, Fontanès (FR); Eric Degryse, Crosne (FR); Pedro Vico, Eschau (FR); Richard Lathe, Edinburgh (GB)

(73) Assignee: Transgene S.A., Strasbourg (FR)

( * ) Notice: Subject to any disclaimer, the term of this patent is extended or adjusted under 35 U.S.C. 154(b) by 149 days.

(21) Appl. No.: 10/089,803

(22) PCT Filed: Oct. 4, 2000

(86) PCT No.: PCT/FR00/02753

§ 371 (c)(1),
(2), (4) Date: Jul. 22, 2002

(87) PCT Pub. No.: WO01/25469

PCT Pub. Date: Apr. 12, 2001

(30) Foreign Application Priority Data

Oct. 5, 1999 (FR) .......................... 99 12410

(51) Int. Cl.
| | |
|---|---|
| *C12N 1/18* | (2006.01) |
| *C12N 9/10* | (2006.01) |
| *C12N 15/00* | (2006.01) |
| *C12P 7/02* | (2006.01) |
| *C07H 21/04* | (2006.01) |

(52) U.S. Cl. .................. 435/58; 435/155; 435/189; 435/190; 435/25; 435/69.1; 435/320.1; 435/254.2; 435/193; 435/254.21; 435/56; 536/23.2

(58) Field of Classification Search ................ 435/189, 435/190, 25, 69.1, 155, 320.1, 254.2, 254.21, 435/193, 58, 56; 536/23.2
See application file for complete search history.

(56) References Cited

U.S. PATENT DOCUMENTS 6,218,139 B1  4/2001 Achstetter et al.

FOREIGN PATENT DOCUMENTS

| WO | WO 96/12810 | 5/1996 |
|---|---|---|
| WO | WO 97/37664 | 10/1997 |
| WO | 99/40203 | 8/1999 |

OTHER PUBLICATIONS

Wu et al., Journal of Lipid Research 40:2195–2203, 1999.*
Bork, Genome Research, 10:398–400, 2000.*
Witkowski et al., Biochemistry 38:11643–11650, 1999.*
Seffernick et al., J. Bacteriol. 183(8):2405–2410, 2001.*
K.A. Rose et al., *Proc. Natl. Acad. Sci. USA*, vol. 94, pp. 4925–4930, May 1997.
K.A. Koshcheyenko et al., *Enzyme and Microbial. Technology*, vol. 5, No. 1, pp. 14–21, 1983.
O.P. Ward et al., *Enzyme and Microbial. Technology*, vol. 12, No. 7, pp. 482–493, 1990.
M. Iwasaki et al., *Biochem Journal*, vol. 291, No. 2, pp. 569–573, 1993.
K. Nagata et al., *Journal of Biological Chemistry*, vol. 262, No. 6, pp. 2787–2793, 1987.
K. Athenstaedt et al., *Journal of Biological Chemistry*, vol. 275, No. 1, pp. 235–240, 2000.

* cited by examiner

*Primary Examiner*—Rebecca E. Prouty
*Assistant Examiner*—Delia M. Ramirez
(74) *Attorney, Agent, or Firm*—Burns, Doane, Swecker & Mathis, L.L.P.

(57) ABSTRACT

The invention concerns a novel method for producing hydroxylated and/or acetylated steroid comprising steps which consist in: culturing yeasts on a medium comprising at least a precursor of such hydroxylated and/or acetylated steroids; then isolating the hydroxylated and/or acetylated steroids from the medium after bioconversion. Said method is characterized in that said yeasts are yeasts transformed so as to express the product of Cyp7b gene. The invention also concerns the modified yeast strains.

10 Claims, No Drawings

SEQUENCE LISTING

<160> NUMBER OF SEQ ID NOS: 4

<210> SEQ ID NO 1
<211> LENGTH: 35
<212> TYPE: DNA
<213> ORGANISM: Artificial sequence
<220> FEATURE:
<223> OTHER INFORMATION: Description of the artificial sequence: Primer
      for amplification of cyp7b

<400> SEQUENCE: 1
gatcgtcgac aaaaatgtct ggagccacga cccta                              35

<210> SEQ ID NO 2
<211> LENGTH: 25
<212> TYPE: DNA
<213> ORGANISM: Artificial sequence
<220> FEATURE:
<223> OTHER INFORMATION: Description of the artificial sequence: Primer
      for amplification of cyp7b

<400> SEQUENCE: 2
gatcacgcgt tttcagcttc tccaa                                         25

<210> SEQ ID NO 3
<211> LENGTH: 36
<212> TYPE: DNA
<213> ORGANISM: Artificial sequence
<220> FEATURE:
<223> OTHER INFORMATION: Description of the artificial sequence:Primer
      to isolate gene yil124w of saccharomyces
      cerevisiae

<400> SEQUENCE: 3
gactgtcgac aagtatgtcg gagttacagt cacaac                             36

<210> SEQ ID NO 4
<211> LENGTH: 30
<212> TYPE: DNA

-continued

```
<213> ORGANISM: Artificial sequence
<220> FEATURE:
<223> OTHER INFORMATION: Description of the artificial sequence:Primer
      to isolate gene yil124w of saccharomyces
      cerevisiae

<400> SEQUENCE: 4
ctacacgcgt ggtgtacaaa ctatacggaa                                      30
```

METHOD FOR PREPARING STEROIDS MODIFIED BY YEAST FERMENTATION

The present invention relates to a novel method for producing hydroxylated and/or acetylated steroids by yeast fermentation.

Steroids, in particular cholesterol-derived steroids, are involved in many physiological processes, among which mention may be made of the regulation of carbohydrate and cholesterol levels in the circulating blood, the maintenance and development of muscle mass and the development of the central nervous system.

Among the drawbacks observed in the event of an imbalance in circulating steroid levels, mention may be made of the possible triggering of autoimmune diseases, such as lupus, of certain cancers, for example breast cancer, and of cardiovascular diseases, for example atherosclerosis. Problems with steroid regulation are also suspected in the case of the triggering of certain neurological diseases, such as Parkinson's disease or Alzheimer's disease.

The studies carried out, in particular by Professor Baulieu, on dehydroepiandrosterone, or DHEA, have shown the importance of steroids, in particular neuro-steroids, in the development of the central nervous system, but also the possible impact of this type of steroid in all the closely related processes, including the phenomenon of aging (Baulieu and Robel, 1998, Proc. Natl. Acad. Sci., 95, 4089–4091).

It is therefore particularly advantageous to be able to have novel steroid derivatives, in particular of the neurosteroid family, which are involved in a very large number of physiological processes.

This is precisely one of the subjects of the present invention, namely the development of a method allowing access to novel steroid derivatives, in particular neurosteroids, using fermentation methods which permit high specificities and also considerable production yields.

The methods according to the present invention may, moreover, be used in order to obtain steroids which have a structure which is also known, but which, to date, were difficult to access using commercially acceptable methods.

The present invention is based on the demonstration of the fact that yeasts are capable of biologically converting, or bioconverting, precursor steroids, producing diverse hydroxylated and/or acetylated steroids which can, of course, if necessary, then be modified on such particularly reactive functions.

For this reason, the present invention relates in particular to a method for producing hydroxylated and/or acetylated steroids, comprising the steps according to which:

yeasts are cultured on a medium comprising at least one precursor of such hydroxylated and/or acetylated steroids, and then the hydroxylated and/or acetylated steroids are isolated from the medium after bioconversion, said method being characterized in that said yeasts are yeasts transformed so as to express the product of the Cyp7b gene.

Yeast naturally possesses an enzymatic acetylation activity encoded by the atf2 gene and an enzymatic dehydrogenation activity encoded by the yil124w gene. The enzyme encoded by the atf2 gene (the sequence and activity of which are described in Cauet et al., 1999, Eur. J. Biochem., 261, 317–324 and in French patent application FR2774393 or at the address genome-www.stanford.edu/ *Saccharomyces*) is acetyl coenzyme A-pregnenolone acetyltransferase, hereafter named "APAT". This enzyme allows the esterification, and more particularly the acetylation, of a steroidal precursor, such as for example a $\Delta^5$— or $\Delta^4$—3β-hydroxysteroid, for instance pregnenolone, 17-hydroxypregnenolone, dehydroepiandrosterone (DHEA) or 4-pregnen-3β-ol-20-one, for example. This esterification is preferably carried out on the OH function in position 3 of a said precursor. Expression of this activity in yeasts consequently makes it possible to produce derivatives of steroidal precursors which are completely or partially acetylated. Similarly, it is possible to chemically protect all or some of the OH functions of the precursor incorporated into the culture medium, such that the acetylation reaction may not take place on all or some of said functions. Such protection methods are well known and consist, for example, of addition of silane, of modification to an ester function, etc.

However, according to a particular embodiment of the present invention described hereafter, it is also possible to use yeast strains lacking the APAT enzymatic activity, such as in particular those described in Cauet et al. (1999, Eur. J. Biochem., 261, 317–324) or in French patent application FR2774393, the contents of which are incorporated into the present application by way of reference.

The yil124w gene was described during the yeast genome sequencing project, but its function had not then been determined. It is located on chromosome IX, at the coordinates 126204 to 127097. Its sequence is readily accessible to those skilled in the art in the database for the *Saccharomyces* genome, located, for example, at the address genome-www.stanford.edu/. In the context of the studies of the present invention, it has been shown that the protein encoded by the yil124w gene has dehydrogenase activity comparable to the activity of the 17β-hydroxysteroid dehydrogenase previously described in mammals (17BDH; Wu et al., 1993, J. Biol. Chem., 268, 12964–12969). This activity more specifically directs the reduction, to alcohol, of the ketone function located, naturally or after chemical modification, in position 17 of certain steroidal precursors, such as DHEA for example. More particularly, in the case of the DHEA substrate, the enzymatic activity of the protein encoded by the yil124w gene leads to the reduction of the ketone function of this steroid and to the formation of a 3,17-diol, hereafter referred to as "Diol". In addition, when made necessary, since the sequence of the yil124w gene is known, it is easy for those skilled in the art, familiar with techniques for mutagenesis in yeast, to produce a yeast strain in which the yil124w gene is inactivated. For example, in accordance with the examples which follow, it is possible to obtain yeast strains for which the sequence encoding the yil124w gene has been knocked out (knock-out technique) and the enzymatic activity suppressed.

The Cyp7b gene is known; it has already been described by Stapleton et al., (1995, J. Biol. Chem., 270, 29739–29745) or Rose et al. (1997, Proc. Natl. Acad. Sci. USA, 94, 4925–4930). Its sequence is in particular described in patent application WO9612820 and is accessible from the Institute for Fermentation Osaka (IFO) under the accession code IFO 2031. The contents of those documents are incorporated into the present application by way of reference. However, there was nothing to imply that this mammalian gene could be expressed, and more particularly expressed in its active form, by a yeast. In addition, there was nothing which made it possible to envision that such a yeast would be capable of using a steroid as a substrate. Specifically, the Cyp7b gene is a gene isolated from mammals, in particular rats, mice and humans, in which the enzyme encoded by this gene belongs to the family of enzymes commonly named "cytochrome P450s", the active form of which contains heme (Poulos, 1988, Pharm. Res., 5, 67–75) and which are involved in the metabolic pathways for steroids (see Rose et al., 1997, Proc. Natl. Acad. Sci. USA, 94, 4925–4930). The Cyp7b protein is a hydroxylase, and more particularly a 7-hydroxylase, which makes it possible to obtain 7-hydroxylated steroids, and more particularly 7α-hydroxylated steroids. However, it is possible to envision the particular case for which the steroidal substrate is an equivalent of the known steroidal compounds, in which, by modification of the structure of one of the rings, the "position which is naturally 7" is transformed into a "position 6 equivalent". In this specific case, the Cyp7b protein would make it possible to obtain 6-hydroxylated steroids.

According to a preferred case of the invention, the action on the "Diol" compound described above of the Cyp7b enzyme expressed in the yeasts used allows the formation of a 3,7,17-triol, hereafter named "Triol". In addition, when the 3-OH function of said diol or of said triol is acetylated, reference will be made, respectively, to an "acetyl-diol" or "acetyl-triol".

The nature of the hydroxylated and/or acetylated steroids produced according to the method of the invention consequently depends on the possibility of the yeast expressing or not expressing the functions of acetylation encoded by the atf2 gene and/or of dehydrogenation encoded by the yi1124w gene, in combination with the possibility of said yeast expressing the Cyp7b hydroxylation enzyme.

The compounds the production of which according to the present invention will be desired will preferably be hydroxylated compounds since, for a large number of steroids, it has been shown that the hydroxylated derivative is more active than the acetylated derivative. However, in this respect, it should be noted that the acetyl function can be gradually hydrolyzed in vivo and may therefore constitute a delayed form of the hydroxylated form (i.e. the compound as administered to the patient is not the active form, but this active form is obtained in vivo after natural metabolizing of the acetylated compound). For this reason, the present invention relates both to a method for producing steroids comprising free OH functions and to one of producing steroids comprising OH functions protected with an acetyl radical.

In any event, according to the preferred embodiment for which the production of hydroxylated steroidal derivatives is sought, it is desirable for the APAT activity of the yeast used in the method of the invention to be low or zero. There are various possibilities for accomplishing this.

According to a first variant, it is possible to use yeast strains in which the atf2 gene is naturally absent or, at the very least, is expressed very little or not at all. Thus, Nagasawa et al. (Biosci. Biotechnol. Biochem. 62, 1852–1857, 1998) mention that a strain IFO2031 (*Saccharomyces bayanus*) lacks the atf2 gene.

According to another variant, it is possible to use culture conditions in which the ability of the yeasts to acetylate the steroidal precursor(s) present in the culture medium is greatly decreased, or even eliminated. In particular, the applicant has demonstrated the fact that strains having the atf2+ activity carry out more limited acetylation reactions under conditions which are oxidative, in particular by growth on non-fermentable carbon sources, such as for example glycerol or acetate.

According to a third variant, it is also possible to use yeast strains which have, naturally or after genetic manipulation, deacetylase activity. This activity has been described as acting on short-chain alcohol esters (rEF). The use of such a system would make it possible to deacetylate the products obtained by the APAT activity.

Finally, it is possible to use atf2⁻ strains, i.e. strains in which the gene is not expressed or in which the product of this gene is inactive. More particularly, those skilled in the art are capable, via routine experiments, of preparing yeast strains lacking the APAT enzymatic activity, such as in particular those described in Cauet et al. (1999, Eur. J. Biochem., 261, 317–324) or in French patent application FR2774393, the contents of which are incorporated into the present application by way of reference.

Similarly, it may be advantageous to induce the activity of the atf2 gene only at a certain moment of the method of the invention, for example sequentially to the expression of the Cyp7b gene. Thus, certain promoters have been described in yeast which are active only in the presence of an outside stimulus (Guarente et al., 1982, Proc. Natl. Acad. Sci., 79, 7410–7414) or when the yeasts are in the stationary phase (Panaretou et al., 1992, Eur. J. Biochem., 206, 635–640). The use of an atf2 gene placed under the control of such a promoter consequently makes it possible to control the APAT activity in the yeast containing such a recombined gene.

Similarly, the presence in the yeast used in the method of the invention of an endogenous activity similar to the 17BDH activity of mammals (encoded by the yi1124w gene) leads to the formation of reduced compounds which may provide an additional value compared to the unmodified product. On the other hand, it may also be desirable to have yeast strains or culture conditions for which the activity of the yi1124w gene is decreased or suppressed. Thus, it is possible to make use of conditions for culturing in oxidative medium or of yeast strains in which the yi1124w gene has been inactivated.

Of course, according to preferred cases of the invention, for which it is advantageous to obtained reduced compounds, it is possible to have yeast strains capable of overexpressing the yi1124w gene or of expressing the 17BDH activity at a preferred moment of the bioconversion, for example by using strains for which the yi1124w gene is placed under the control of an inducible promoter, such as those described above.

It is, of course, possible also to modify the acetyl function obtained after the action of the APAT activity during the method of the invention using an atf2+ yeast strain, for example by transforming said yeast strain so that it also expresses an enzymatic activity which reacts on this substrate. When the gene in question encodes an enzyme with methylase activity, methylated steroidal derivatives can thus be obtained.

Among the steroid precursor substrates which can be used in the present invention, mention should be made of the steroids or steroid precursors which have a 7 position which can be hydroxylated, i.e. which is accessible and can be hydroxylated by an enzyme having hydroxylase activity. Examples of such positions which can be hydroxylated consist in particular of a carbon, a sulfur and a nitrogen.

Among the steroid precursor substrates which can be used in the present invention, mention should be made more particularly of the 3-hydroxylated steroids, and in particular the 3-β-hydroxylated steroids, or the steroids which have a 3-keto function.

More particularly, without this list being limiting, in this invention, consideration will be given to a precursor selected from the group consisting of the steroids with a structure of the androstane, androstene, pregnane, pregnene, cholane, cholene, cholesterol, ergostane, ergostene, testosterone or stigmastane type, for example DHEA, testosterone, pregnenolone, pregnanolone, 25-hydroxycholesterol, 5-α-androstane-3β, 17β-diol or 5-α-androstene-3β, 17β-diol.

Of course, these compounds may also be obtained in acetylated form. In precursors which have a ketone function in position 17, this function can also undergo reduction, as has been described previously.

The invention may be implemented by using yeasts of various genera which may be selected, without this list being limiting, from *Candida, Yarrovia, Kluyveromyces, Schizosaccharomyces, Torulopsis, Pichia* and *Hansenula*.

A preferred embodiment of the invention will use yeasts of the genus *Saccharomyces*, for example *S. cerevisiae*.

The conditions under which these yeasts can be cultured are known to those skilled in the art; it is sufficient to add a substrate which is a precursor for the desired steroids to the culture medium in order to carry out the method according to the present invention.

The examples provided below show that some media are more favorable to the production of hydroxylated steroids than others; this is a parameter which can be readily optimized by those skilled in the art.

Among the media, mention should be made of YPD, YPG, YNBD and YNBG containing in particular glycerol and/or glucose (see also Sherman, 1991, Methods Enzymol., 194, 3–21). Similarly, it is possible to adjust the composition of the medium during the method or to select the medium as a function of the promoter selected to direct the expression of the Cyp7b gene (for example, the minimal medium YNBD will be chosen in the case of the CYC1 promoter and the rich medium YPG will be selected in the case of the TEF1 promoter).

The additional culture conditions are the usual conditions, but they can be optimized.

The amounts of precursor added to the culture medium in the context of the method of the invention will be chosen so as to obtain a concentration in the bioconversion medium of between 10 and 200 μg/ml, preferably between 20 and 100 μg/ml.

The yeasts used in the context of the invention are strains transformed so as to express the product of the Cyp7b gene. This means that said strains have been modified beforehand so as to introduce the Cyp7b gene into the yeasts and allow its expression. With regard to the transformation of the yeasts in order to express the Cyp7b gene, it is possible to introduce this gene either into the genome of the yeast or such that it has an extrachromosomal location. For these purposes, circular or linear systems of the plasmid type may be used. Among the plasmids comprising origins of replication from yeast, mention may be made of the plasmids derived from the 2μ plasmid of *Saccharomyces*, which will preferably comprise, as a selectable marker, either a selectable marker of resistance to antibiotics, for example the G418R gene, or at least one auxotrophy marker, such as URA3, URA3d or LEU2. Such transformation techniques are well-described in the literature and do not present any particular difficulty.

With regard to the Cyp7b gene, its nucleic acid sequence (Institute for Fermentation Osaka (IFO), accession code IFO 2031 or SEQ ID NO. 1) may be cloned under the control of a yeast promoter, such as CYC1 (Degryse et al. Yeast (1995), 11, pp. 629–640), TEF1 (Cotrelle et al., 1985, J. Biol. Chem., 260, 3090–3096) or TDH3 (Bitter and Egan, 1984, Gene, 32, 263–274), in order to allow its expression in the transformed yeasts.

The method of the invention also comprises a step according to which the steroids produced are isolated from the medium. Such a step does not constitute a crucial element of said method and may implement various techniques generally used in the domain of steroid purification (chromatography, HPLC, etc.).

The invention also relates to the novel hydroxylated steroids which may be, or which are, obtained using the method described above, and also to their use in the context of therapeutic or prophylactic applications, in particular as neurosteroids, for preparing a medicinal product intended to treat the human or animal body.

It also relates to compositions, in particular pharmaceutical compositions, containing such novel hydroxylated steroids. These pharmaceutical compositions also contain one or more support(s) acceptable from a pharmaceutical point of view. Such a support is preferably isotonic, hypotonic or weakly hypertonic and has a relatively low ionic strength, such as for example a sucrose solution. Moreover, such a support may contain any solvent or aqueous or partially aqueous liquid, such as nonpyrogenic sterile water. The pH of the formulation is also adjusted and buffered in order to correspond to the requirements of use in vivo. The formulation may also include a diluent, an adjuvant or an excipient which is acceptable from a pharmaceutical point of view, and also solubilizing, stabilizing and/or preserving agents. For an injectable administration, preference is given to a formulation in aqueous, nonaqueous or isotonic solution. It may be provided in a single dose or in multiple doses in liquid form or dry form (powder, lyophilizate, etc.) which can be reconstituted extemporaneously with a suitable diluent.

The examples below will make it possible to understand the methods for constructing the vectors and for transforming the yeasts, but this involves, for the most part, technology which is already known to those skilled in the art. The vectors are described in Degryse et al. (Yeast (1995), 11, pp. 629–640).

It is understood that the results below are given only by way of examples. Thus, the levels obtained, for example in the bioconversion manipulations, are only given by way of indication and in no way represent a claim of the maximum capacity of the system under optimized conditions.

EXAMPLE 1

Construction of Expression Vectors for the cyp7b cDNA

The cyp7b cDNA is amplified using the oligo of sequence SEQ ID No. 1, thus introducing a SalI site (underlined) and a sequence of 4As before the ATG codon, and a second primer of sequence SEQ ID No. 2 introducing a MluI site after the stop codon.

The first PCR product is subcloned, after SalI/MluI restriction, into the SalI/MluI site of the vector equivalent to pTG10164 (Degryse et al., Yeast (1995), 11, pp. 629–640). This produces a vector pTG14010 containing the Cyp7b gene under the control of the CYC1 promoter (Degryse et al. Yeast (1995), 11, pp. 629–640) in a 2μ environment and with the G418R (neo) gene.

Next, the TEF1 promoter (Cotrelle et al., 1985, J. Biol. Chem., 260, 3090–3096) is cloned by ClaI/SalI exchange, which produces the vector pTG14011; the corresponding plasmids are described in the above-mentioned Yeast article.

The NotI expression block containing the CYC1 (respectively, TEF1) promoter was introduced into the 2 micron-based plasmid pTG10042 (respectively, pTG10092) containing the URA3d gene, by the recombination method already described in the Yeast article, to give the plasmid pTG14012 (respectively, pTG14014). The pTG14015 plasmid was constructed in the same way as pTG14014, from pTG10220, which carries the URA3 gene, as a selectable gene.

The URA3d gene was chosen because it leads to selection for a very large number of copies in minimal medium. The URA3 gene produces an average number of copies and the selection pressure is reasonable in minimal medium.

The pTG14012, pTG14014 and pTG14015 plasmids were introduced by transformation into the FY1679-28c strain and the transformants were selected on a suitable minimal medium and then stored.

The table below provides a summary of the expression vectors for cyp7b:

| PLASMID | PROMOTER | SELECTABLE MARKER |
|---------|----------|-------------------|
| pTG14011 | TEF1 | G418R |
| pTG14012 | CYC1 | URA3d |
| pTG14014 | TEF1 | URA3d |
| pTG14015 | TEF1 | URA3 |

All the vectors contain the E. coli replicon and the origin of replication of the yeast 2µ plasmid.

The yeasts used are:

FY1679-28c (Mata ura3-52 trpl-63 leu2-1 his3-200 GAL fen1), a Mata segregant from FY1679.

TGY202 and TGY206 are TRP1 derivatives obtained after transformation of the strains F1679-28c and TGY186, respectively.

In TGY156, part of the atf2 gene has been inactivated and replaced with URA3. TGY186 is a derivative of TGY156 in which the URA3 gene at the atf2 locus has been replaced with TEF1::PGK1 in the form of an expression block.

The strains are transformed using the lithium acetate procedure (Ito, et al., 1983, J. Bact. 153, 163–168) or electroporation (Nacken et al., 1994, Nucleic Acids Res, 22, 1509–10), and selected on a YNBG solid medium containing the suitable amino acids.

EXAMPLE 2

Bioconversion

The cells are grown on a YNBG solid medium supplemented with the suitable amino acids. A preculture is effected for 24 hours at 28° C. in a medium which has the same composition as the culture medium to be tested. The minimal medium (YNB and the carbon source) is supplemented with 0.5% of casamino acids (in addition to the nutrients required for the strain).

When the growth medium contains glycerol (2%), glucose is also present at 0.1% in order to initiate the culture.

An aliquot of the preculture is used to inoculate 10 ml of culture medium with an optical density at 600 nm of 0.1 and DHEA is solubilized in a 50/50 tergitol/ethanol mixture at 10 mg/ml (or added at the time indicated). At various time periods, a 500 µl aliquot of the culture medium is taken and the steroids are extracted in order to assay them.

4 ml of dichloromethane are added to the culture medium, and the mixture is vortexed for 10 minutes and centrifuged for 3 minutes at 3000 rpm. The organic phase is dried under a stream of nitrogen at 50° C. 500 µl of dichloromethane are added to the residue, and the sample is vortexed rapidly and then dried as above. The residue is taken up in a 90/10 isopropanol/water mixture and transferred into injection tubes, which are sealed. The sample is analyzed by HPLC against standards composed of DHEA, 7-hydroxy-DHEA and acetyl-DHEA. Some standards also contain 5-androstene-3β, 17β-diol.

The various culture media which were used are YPG, YNBD (glucose at 2%) and YNBG (glycerol at 2%, glucose at 0.1%).

The results obtained are given in the examples below;

EXAMPLE 3

Demonstration of an Intrinsic 17-dehydro-genase Activity in Yeast

Incubation of TGY202 and acetyl-DHEA for 49 hours in YNBD made it possible to isolate acetyl-diol, indicating dehydrogenase activity in the yeast.

The characterization of the product obtained made it possible to determine that this activity is similar to that of mammalian 17β-hydroxysteroid dehydrogenase (17BDH).

EXAMPLE 4

Identification of the yi1124w Gene Encoding the 17BDH Activity of the Yeast *Saccharomyces cerevisiae*

The yi1124w gene was amplified by PCR using the primers of sequences SEQ ID No. 3 and SEQ ID No. 4, which introduce, respectively, SalI and MluI restriction sites. The amplification product, after restriction with the SalI and MluI enzymes, was subcloned into the yeast vector pTG10851 to give the vector pTG14491. The yi1124w gene is thus under the control of the yeast promoter TEF1 and of the yeast terminator PGK1. The origin of replication is 2-micron and the selectable marker is the G418-resistance gene.

After transformation of TGY206 with pTG14491, bioconversion is carried out for 24 hours in the YNBD medium, using DHEA as the substrate. The steroids present in the culture medium are analyzed:

|  | DHEA | Diol |
|---|------|------|
| TGY206 | 62 | 13 |
| TGY206-pTG14491 | 27 | 52 |

The values are expressed in µg/ml of the steroid extracted from the culture medium.

These results confirm the 17BDH activity of the yi1124w gene, and show that overexpression thereof makes it possible to produce reduced steroidal derivatives.

EXAMPLE 5

Generation of a Knock-out Mutant for the yi1124w Gene

The pTG14491 plasmid was restricted with PstI and NcoI (unique restriction sites in the coding sequence of yi1124w) and the sticky ends were made blunt with T4 DNA polymerase. The URA3 gene is then cloned into this plasmid such that the coding sequence of yi1124w is knocked out by this selectable marker URA3. The resulting plasmid, pTG14584, contains the URA3 gene in the same direction of translation as the TIL124w gene. After restriction of pTG14584 with SalI and MluI, the fragment released containing yi1124w knocked out by URA3 is introduced into the TGY202 and TGY206 strains, and the recombinant colonies are selected on YNBD+LH, the selection being for prototrophy for uracil. The TGY279 and TGY282 strains, respectively, are thus obtained.

The TGY206 and TGY282 strains are incubated in the presence of DHEA or acetyl-DHEA in the YNBD medium for 24 h and the products obtained are measured.

| Products | DHEA | Acetyl-DHEA | Diol | Acetyl-diol |
|---|---|---|---|---|
| DHEA substrate | | | | |
| TGY206 | 56 | 0 | 43 | 0 |
| TGY282 | 86 | 0 | 0 | 0 |
| Acetyl-DHEA substrate | | | | |
| TGY202 | 4 | 34 | 7 | 20 |
| TGY282 | 16 | 46 | 0 | 0 |

Results expressed in μg/ml extracted from the culture medium.

It clearly appears, therefore, that the TGY282 strain is no longer capable of reducing the DHEA or acetyl-DHEA to, respectively, diol or acetyl-diol. This confirms the inactivation of the yil124w gene and also of its 17-dehydrogenase function.

Moreover, it may be observed that the yeast has an intrinsic activity of deacetylation of acetyl-DHEA to DHEA. Thus, identification of the gene responsible and its overexpression relative to the APAT activity will make it possible to produce steroids without using mutants of the atf2 gene.

EXAMPLE 6

Use of the Method According to the Present Invention to Obtain 7-hydroxy-DHEA from DHEA Using the TGY202 Strain Transformed with the Expression Plasmids for cyp7b The TGY202 strain transformed with the pTG14012, pTG14014 or pTG14015 plasmid is incubated in the presence of DHEA (40 μg/ml) in a YPG medium, for 48 hours, and the presence of 7-hydroxy-DHEA (7αHO-DHEA) in the medium is evaluated.

The results are given in the table below:

| TGY202 | 7-HYDROXY-DHEA |
|---|---|
| pTG14012 | 4.2 |
| pTG14014 | 6.4 |
| pTG14015 | 3.1 |

The presence of 7αHO-DHEA in the medium indicates that the cyp7b gene is expressed in an active form which allows the bioconversion of the DHEA to 7αHO-DHEA by the yeast. Thus, any potential substrate for Cyp7b may be hydroxylated in vivo by a yeast strain expressing cyp7b.

Moreover, these results indicate that the TEF1 promoter is more effective than CYC1, and that the selectable marker URA3d gives better results than the marker URA3.

EXAMPLE 7

Increase in the Production of 7αHO-DHEA by Bioconversion, by Modulation of the Fermentation Conditions TGY202-pTG14012 and TGY202-pTG14014 are incubated in the YNBD and YNBG media for 48 hours, in the presence of DHEA (40 μg/ml) added to the medium immediately after inoculation or after 8 hours of incubation.

The results are given in the following table (as % of product accumulated).

| Medium | YNBD TGY202-pTG14012 | TGY202-pTG14014 | YNBG TGY202-pTG14012 | TGY202-pTG14014 |
|---|---|---|---|---|
| DHEA (40 μg/ml) added at t 0 | | | | |
| Acetyl-DHEA | 20.1 | 9.6 | 65.2 | 55.8 |
| Acetyl-diol | | | | |
| Acetyl-triol | | | | |
| DHEA | 0 | 0 | 5.7 | 1.1 |
| Diol | 0 | 2.9 | 0 | 0 |
| 7αHO-DHEA | 52.3 | 35.6 | 25.1 | 37.2 |
| Triol | 27.5 | 51.9 | 4.0 | 5.4 |
| DHEA (40 μg/ml) added at t 0 + 8 hours | | | | |
| Acetyl-DHEA | 3.0 | 2.0 | 25.1 | 0 |
| Acetyl-diol | | | | |
| Acetyl-triol | | | | |
| DHEA | 0 | 0 | 17.3 | 3.4 |
| Diol | 1.5 | 0 | 7.4 | 0 |
| 7αHO-DHEA | 40.6 | 53.1 | 36.9 | 81.5 |
| Triol | 54.9 | 44.9 | 13.3 | 15.1 |

It is thus noted that the fermentation medium and the time at which the DHEA substrate is added have an influence on the selective production of 7αHO-DHEA, a delayed inoculation generally giving better results, and the YNBG medium being superior to the other media.

EXAMPLE 8

Preferential Production of 7αHO-DHEA in the Absence of Acetylated Derivatives by Using KO Strains for APAT Activity TGY206p-pTG14014 is incubated in YNBD in the presence of DHEA (100 μg/ml) for 49 hours.

The analysis of the products obtained indicates that 100% of 7αHO-DHEA is recovered (91.7 μg/ml).

When the culture medium is YNBG, a mixture of 7αHO-DHEA (89%, 73.8 μg/ml), triol (6%, 5 μg/ml) and DHEA (5.3%, 4.4 μg/ml) is obtained.

These observations indicate that, in the absence of APAT activity, the production of acetylated derivatives is avoided. On the other hand, the presence of the intrinsic 17BDH activity leads to a contaminating presence of Diol or Triol.

EXAMPLE 9

Preferential Production of Triol

Incubation of TGY206p-pTG14014 in the presence of Diol (100 μg/ml) for 48 hours leads to the production of 26.4 μg/ml Triol (36%) of the final products, 74% of Diol remaining) in YNBG. The use of YNBD gives a bioconversion rate of 100%.

These results show that, by changing the fermentation medium, it is possible to channel the production of metabolites from a substrate. In particular, it may be readily envisioned that overexpression of the yil124w gene allows rapid and/or complete accumulation of reduced derivatives. By coupling this overexpression with that of cyp7b, it is thus possible to achieve virtually complete conversion to Triol, from DHEA as the starting substrate.

EXAMPLE 10

Preferential Production of Acetyl-DHEA using a Yeast Strain which is a KO Strain for 17BDH Activity The TGY202 and TGY279 strains were incubated with DHEA for 24 hours in the YPD culture medium, and the steroids produced were measured.

|        | DHEA | Ac-DHEA | Diol | Ac-Diol |
|--------|------|---------|------|---------|
| TGY202 | 1    | 84      | 14   | 1       |
| TGY279 | 3    | 96      | 0    | 1       |

Results expressed as percentage of the total of the steroids extracted from the culture medium.

It clearly appears that the TGY279 strain virtually completely transforms the DHEA to acetyl-DHEA, in the absence of the 17BDH activity.

EXAMPLE 11

Exclusive Production of 7αHO-DHEA Using the TGY282 Strain, which is a KO Strain for the APAT and 17BDH Activities and Expresses cyp7b The TGY279 and TGY282 strains are transformed with the pTG14011 plasmid and selected on YPG+G418. Incubation of the transformed strains in the YPD medium for 24 hours, using DHEA as the substrate, makes it possible to measure the levels of steroids produced by these strains.

|                  | DHEA | Ac-DHEA | Diol | Ac-Diol | 7αHO-DHEA |
|------------------|------|---------|------|---------|-----------|
| TGY279-pTG14011  | 3    | 49      | 1    | 0       | 47        |
| TGY282-pTG14011  | 31   | 0       | 1    | 0       | 68        |

Results expressed as percentage of the total of the steroids extracted from the culture medium.

Although the bioconversion did not go to completion in this experiment, it is seen that the TGY282-pTG14011 strain produces exclusively 7αHO-DHEA from DHEA, whereas a strain also containing the APAT activity produces not only 7αHO-DHEA, but also acetyl-DHEA.

---

What is claimed is:

1. A method for producing hydroxylated and/or acetylated steroids, comprising the steps according to which:
   yeast cells are cultured on a medium comprising at least one precursor of such hydroxylated and/or acetylated steroids, and then
   the hydroxylated and/or acetylated steroids are isolated from the medium after bioconversion, wherein said precursor is dehydroepiandrosterone (DHEA) or pregnenolone;
wherein said yeast cells are *Saccharomyces cerevisiae* cells;
wherein said yeast cells are transformed with the rat Cyp7b gene so as to express the 7α hydroxylase enzymatic activity encoded by said rat Cyp7b gene which catalyzes 7α hydroxylation of pregnenolone and DHEA;
wherein said yeast cells are further modified so as to lack an acetyl coenzyme A-pregnenolone acetyltransferase (APAT) activity when compared to wild type yeast cells; and
   wherein the modification of the yeast cells resulting in a lack of acetyl coenzyme A-pregnenolone acetyltransferase (APAT) activity is caused by the inactivation of the *Saccharomyces cerevisiae* atf2 gene.

2. The method of claim 1, wherein said precursor can be hydroxylated at position 7.

3. The method of claim 1, wherein said yeast cells also produce a protein having dehydrogenase activity.

4. The method of claim 3, wherein said dehydrogenase activity is a 17β-hydroxysteroid dehydrogenase activity which catalyzes the production of a steroid precursor hydroxylated at position 17.

5. The method of claim 4, wherein said 17β-hydroxysteroid dehydrogenase activity is encoded by the yil124w gene.

6. The method of claim 1, wherein the yeast cells further lack a 17β-hydroxysteroid dehydrogenase activity when compared to wild type yeast cells.

7. The method of claim 1, wherein the rat Cyp7b gene is under the control of a yeast promoter chosen from the group consisting of CYC1, TEF1 and TDH3.

8. A *Saccharomyces* yeast cell transformed with the rat Cyp7b gene so as to express the 7α hydroxylase enzymatic activity encoded by said rat Cyp7b gene, wherein said yeast cell is further modified so as to lack an acetyl coenzyme A-pregnenolone acetyltransferase (APAT) activity when compared to wild type yeast cells; wherein the modification of the yeast cells resulting in a lack of acetyl coenzyme A-pregnenolone acetyltransferase (APAT) activity is caused by the inactivation of the *Saccharomyces cerevisiae* atf2 gene; and wherein the yeast cells are *Saccharomyces cerevisiae* cells.

9. The method of claim 6, wherein said 17α-hydroxysteroid dehydrogenase activity is that encoded by the yil124w gene.

10. The method of claim 9, wherein the lack of a 17β-hydroxysteroid dehydrogenase activity results from inactivation of the yil124w gene encoding said 17β-hydroxysteroid dehydrogenase activity.

* * * * *